(12) United States Patent
Vekselman et al.

(10) Patent No.: US 12,154,750 B2
(45) Date of Patent: Nov. 26, 2024

(54) SYSTEMS, DEVICES, AND METHODS FOR ION BEAM MODULATION

(71) Applicant: TAE TECHNOLOGIES, INC., Foothill Ranch, CA (US)

(72) Inventors: Vladislav Vekselman, Lake Forest, CA (US); Alexander Dunaevsky, Corona, CA (US); Andrey A. Korepanov, Foothill Ranch, CA (US)

(73) Assignee: TAE TECHNOLOGIES, INC., Foothill Ranch, CA (US)

( * ) Notice: Subject to any disclaimer, the term of this patent is extended or adjusted under 35 U.S.C. 154(b) by 461 days.

(21) Appl. No.: 17/356,171

(22) Filed: Jun. 23, 2021

(65) Prior Publication Data

US 2022/0084774 A1 Mar. 17, 2022

Related U.S. Application Data

(60) Provisional application No. 63/044,314, filed on Jun. 25, 2020.

(51) Int. Cl.
   *H05H 5/06* (2006.01)
   *H01J 27/02* (2006.01)

(52) U.S. Cl.
   CPC .......... *H01J 27/028* (2013.01); *H01J 27/022* (2013.01); *H05H 5/063* (2013.01); *H01J 2237/06375* (2013.01)

(58) Field of Classification Search
   None
   See application file for complete search history.

(56) References Cited

U.S. PATENT DOCUMENTS

| | | | |
|---|---|---|---|
| 4,812,775 A | 3/1989 | Klinkowstein et al. | |
| 5,440,210 A * | 8/1995 | Bogaty | H05H 7/00 348/380 |
| 8,723,451 B2 | 5/2014 | Heid | |
| 9,981,147 B2 | 5/2018 | Lee et al. | |
| 2015/0265854 A1* | 9/2015 | Balakin | A61N 5/107 600/1 |
| 2016/0329201 A1* | 11/2016 | Haufler | H01J 49/26 |

FOREIGN PATENT DOCUMENTS

| | | |
|---|---|---|
| JP | H07 320897 A | 12/1995 |
| JP | 2015 053187 A | 3/2015 |
| WO | WO 2009/142543 A2 | 11/2009 |

OTHER PUBLICATIONS

PCT/US2021/038652 International Preliminary Report on Patentability mailed Dec. 13, 2022.
Schmidt et al., "A 50-mA Negative Hydrogen-Ion Source," IEEE Transactions on Nuclear Science, NS-26(3):4120-4122, (Jun. 1, 1979).
WIPO Application No. PCT/US2021/038652, PCT International Search Report and Written Opinion mailed Oct. 18, 2021.

* cited by examiner

*Primary Examiner* — Eliza W Osenbaugh-Stewart
(74) *Attorney, Agent, or Firm* — ALSTON & BIRD LLP

(57) ABSTRACT

Embodiments of systems, devices, and methods relate to an ion beam source system. An ion source is configured to provide a negative ion beam to a tandem accelerator system downstream of the ion source, and a modulator system connected to an extraction electrode of the ion source is configured to bias the extraction electrode for a duration sufficient to maintain acceleration voltage stability of the tandem accelerator system.

20 Claims, 10 Drawing Sheets

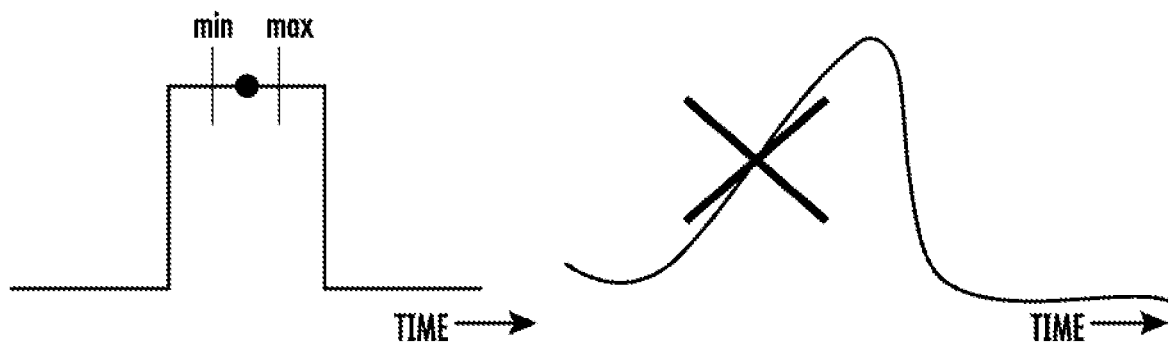
FIG. 5A
FIG. 5B
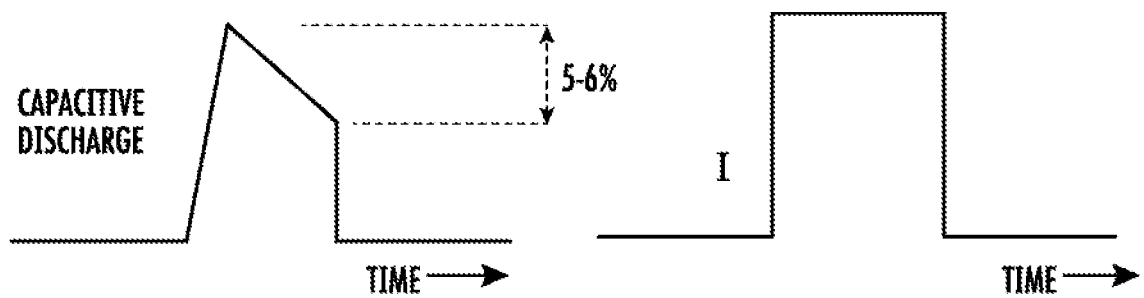
FIG. 6A
FIG. 6B

SYSTEMS, DEVICES, AND METHODS FOR ION BEAM MODULATION

CROSS-REFERENCE TO RELATED APPLICATIONS

The present application claims priority to U.S. Provisional Application Ser. No. 63/044,314, titled "SYSTEMS, DEVICES, AND METHODS FOR ION BEAM MODULATION," filed Jun. 25, 2020, the contents of which are incorporated herein by reference in their entirety.

FIELD

The subject matter described herein relates generally to systems, devices, and methods of modulating beams for use in beam systems.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. A substance that contains boron is injected into a blood vessel, and the boron collects in tumor cells. The patient then receives radiation therapy with neutrons (e.g., in the form of a neutron beam). The neutrons react with the boron to kill the tumor cells without harming normal cells. Prolonged clinical research has proven that a beam of neutrons with an energy spectrum within 3-30 kiloelectronvolts (keV) is preferable to achieve a more efficient cancer treatment while decreasing a radiation load on a patient. This energy spectrum or range is frequently referred to as epithermal.

Most conventional methods for the generation of epithermal neutrons (e.g., epithermal neutron beams) are based on nuclear reactions of protons (e.g., a proton beam) with either Beryllium or Lithium (e.g., a Beryllium target or a Lithium target).

A tandem accelerator is a type of electrostatic accelerator that can employ a two-step acceleration of ion particles using a single high voltage terminal. The high voltage is used to form, e.g., an increasingly positive gradient that is applied to the incoming negative beam to accelerate it, at which point the tandem accelerator converts the negative beam to a positive beam, and then the high voltage is used again to form a reversed decreasingly positive gradient that accelerates (e.g., pushes) the positive beam from the tandem accelerator. Because the high voltage can be used twice, generation of proton beams with a particle energy of 3 MeV typically requires an accelerating voltage of only 1.5 MV, which is within the reach of modern technologies of electrical insulation. Moreover, an ion source of a tandem accelerator is placed at the ground potential, which makes it easier to control and maintain the ion source.

A proton beam provided by a tandem accelerator for the purposes of boron neutron capture therapy (BNCT) has a preferred energy level for treatment efficacy and for use with downstream equipment (e.g., for efficient generation of neutrons on a lithium (Li) target). For a reasonably short treatment time, a particular flux density threshold is required, and with such a requisite threshold comes a minimum proton beam current. A power density associated with such proton beams greatly exceeds the safety limits for materials used in components of a neutron beam system.

Conventional approaches to protecting beam equipment include aligning high power beams at greatly reduced beam current. Beam alignment can work well for beams with relatively low currents, when a shape and position of the beam does not depend on the self-space charge of the beam. However, for tandem accelerators in which beam parameters include a much higher beam current (and where self-space charge has a significant impact on beam shape), alignment of the beam at a reduced current is difficult.

Conventional approaches to protecting beam equipment further include beam modulation for accelerator types such as radio frequency quadrupole (RFQ) accelerators or linear accelerators (e.g., and not tandem accelerators). Beam modulation is used in such applications to reduce the average beam power when the beam current cannot be reduced. This method can be well suited to accelerator types such as RFQs or linear accelerators ("linacs") because beam current is bunched. However, for DC accelerators such as tandem accelerators, modulation has not been applicable because of an inability to change a load of the DC accelerator from zero to nominal and back within a short amount of time.

For these and other reasons, a need exists for improved, efficient, and compact systems, devices, and methods that modulate an ion beam source such that beam power can reduced for safety and preservation of neutron beam system equipment while maintaining treatment efficacy.

SUMMARY

Embodiments of systems, devices, and methods relate to a beam source system capable of modulating a charged particle beam. An ion source is configured to provide a negative ion beam to a tandem accelerator system downstream of the ion source, and a modulator system connected to an extraction electrode of the ion source is configured to bias the extraction electrode for a duration sufficient to maintain acceleration voltage stability of the tandem accelerator system.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 5A illustrates an example desired steady state emission pulse of an ion beam source, for use with embodiments of the present disclosure.

FIG. 5B illustrates an example undesirable steady state emission pulse of an ion beam source.

FIG. 6A illustrates an example desired capacitive discharge curve, for use with embodiments of the present disclosure.

FIG. 6B illustrates an example desired current pulse curve, for use with embodiments of the present disclosure.

DETAILED DESCRIPTION

Figure 1A:
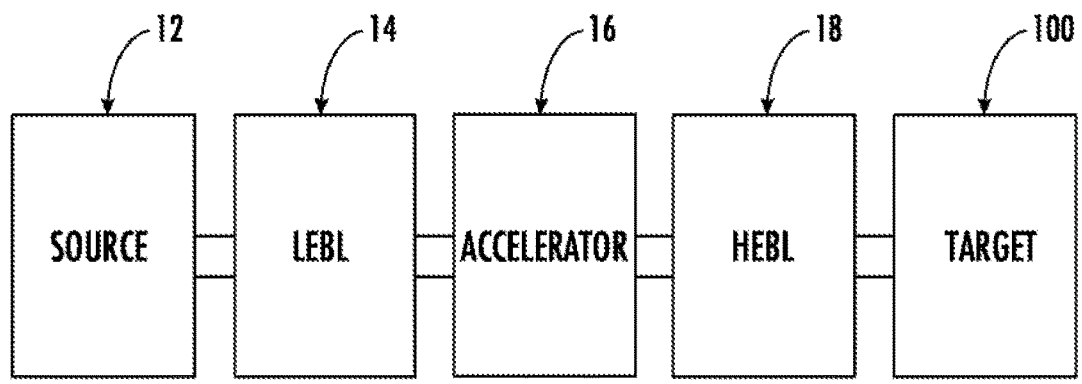
FIG. 1A is a schematic diagram of an example embodiment of a neutron beam system for use with embodiments of the present disclosure.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutron, as well as a species having more than one electron, proton, and/or neutron (e.g., other ions, atoms, and molecules).

Example embodiments of systems, devices, and methods are described herein for an beam source system for use with a beam system (e.g., including a particle accelerator). The embodiments described herein can be used with any type of particle accelerator or in any particle accelerator application involving production of a charged particle beam at specified energies for supply to the particle accelerator.

Embodiments of the present ion beam source system are particularly suited to provide an ion beam, such as a negative particle beam, to a tandem accelerator which also works with a pre-accelerator system. Such a system can be used in numerous applications, an example of which is as a neutron beam system for generation of a neutron beam for use in boron neutron capture therapy (BNCT). For ease of description, many embodiments described herein will be done so in the context of a neutron beam system for use in BNCT, although the embodiments are not limited to just neutron beams nor BNCT applications.

Embodiments described herein decrease an average beam power of the particle accelerator system such that a proton beam with parameters suitable for sources of epithermal neutrons can be provided for boron neutron capture therapy (BNCT) with lithium (Li) or beryllium (Be) targets. That is, embodiments of the present disclosure overcome several disadvantages associated with limitations introduced by equipment and safety in the context of a neutron beam system. A proton beam provided by a tandem accelerator for the purposes of boron neutron capture therapy (BNCT) has a preferred energy level for treatment efficacy and for use with downstream equipment (e.g., for efficient generation of neutrons on a lithium (Li) target). For example, the proton beam can preferably have an energy of 1.9-3.0 megaelectron volts (MeV). For a reasonably short treatment time, a particular flux density threshold is desired, and with such a desired threshold comes a minimum proton beam current (e.g., higher than 5 milliamps (mA)). A power density associated with such proton beams (e.g., proton beams having energies of 1.9-3.0 MeV and current higher than 5 mA) greatly exceeds the safety limits for materials used in components of a neutron beam system (e.g., the neutron generating target, etc.).

By way of further example, at example nominal settings of 2.5 MeV beam energy and 10 mA beam current, the beam power is 25 kilowatts (kW). Given such a large power, it is important to avoid situations where the beam can become misaligned. For a proton beam with a power above 10 kW focused to a location (e.g., a circular or elliptical spot) having a diameter of less than 10 millimeters (mm), the power density likely substantially exceeds the safe limits for materials used in the tandem accelerator (and overall neutron beam system). Any slight deflection of the beam can cause its contact with elements of the beam duct (e.g., within the tandem accelerator) and nearly immediate damage, and possibly destruction, of the elements by the beam.

Advantageously, embodiments of the present disclosure enable modulation of a negative ion beam at the ion beam source by way of modulating an ion extraction voltage. Such modulation results in a limited pulse duration of the negative ion beam such that the average beam power is reduced to a safe level for the materials of the beam system, while at the same time a detectable steady state ion beam is provided to the tandem accelerator without impacting the voltage stability of the tandem accelerator. Accordingly, a proton beam of requisite beam energy and current is provided to downstream components without negatively impacting components of the overall neutron beam system (e.g., beam durations of 10 milliseconds (ms) to 100 ms can result in damage to a neutron generating target downstream from the tandem accelerator).

The desired pulse duration of the negative ion beam (e.g., how long an extraction electrode of the ion beam source should be biased) can be based on a number of factors. While embodiments will vary, generally it is desirable that the pulse duration should be (1) sufficiently long to reach steady state extraction of negative ions of hydrogen (H−) from the plasma of the ion source, and (2) sufficiently short to avoid interference with the voltage stabilization system of the tandem accelerator. In some embodiments, the pulse is short enough in duration to avoid a total discharge of capacitors within the tandem accelerator of greater than 10-15%, and more preferably greater than 5-6%. Accordingly, energy stability of the beam passing through the tandem accelerator is maintained while equipment is protected.

With regard to the pulse being (1) sufficiently long as described above, in some embodiments, a time to reach steady state extraction of negative hydrogen ions for a non-cesiated (e.g., without cesium (Cs)) ion source is 0.1-0.3 ms. In some embodiments, a tandem accelerator has capacitors installed in the outputs of sections of a high voltage rectifier. With regard to the pulse being (2) sufficiently short as described above, in such embodiments when the tandem accelerator is at a nominal 2.5 MeV beam particle energy, a discharge capacitance by propagation of a beam with a current of 10 mA and a duration of one millisecond preferably does not exceed 6%.

Certain embodiments described herein can achieve a desired pulse duration of 0.5-1.0 ms at a frequency of 10 Hz, or a duty cycle of 0.5 to 1%. The duty cycle (active time/total period) will vary based on the operating parameters of the beam system as implemented. For example, the duty cycle can range from 0.1% to 10%. In some embodiments the duty cycle is 1% or less, in other embodiments the duty cycle is 2% or less, in other embodiments the duty cycle is 5% or less, and in still other embodiments the duty cycle is 10% or less.

Preferably, such beam modulation: (a) does not significantly disturb the voltage stabilization of the tandem accelerator; (b) does not discharge capacitors within the tandem accelerator by more than a threshold amount (e.g., 15% or less); (c) provides a beam with a constant maximum output value (e.g., a flat or substantially flat top) for a threshold amount of time (e.g., 2 ms), which is sufficiently long for typical time resolution for a majority of beam diagnostics; and (d) decreases the average beam power substantially to a level safe for the majority of materials used in the beam system as compared to a non-modulated beam. In some embodiments this reduction can be approximately 100 times (to a level of approx. 250 watts (W). In addition to maintaining functionality of the beam system, beam modulation according to embodiments described herein leads to longer term integrity and reliability of beam system materials and components.

Example BNCT Applications

Turning in detail to the figures, FIG. 1A is a schematic diagram of an example embodiment of a beam system 10 for use with embodiments of the present disclosure. In FIG. 1A, beam system 10 includes a source 12, a low-energy beamline (LEBL) 14, an accelerator 16 coupled to the low-energy beamline (LEBL) 14, and a high-energy beamline (HEBL) 16 extending from the accelerator 16 to a target 100. LEBL 14 is configured to transport a beam from source 12 to an input of accelerator 16, which in turn is configured to produce a beam by accelerating the beam transported by LEBL 14 HEBL 18 transfers the beam from an output of accelerator 16 to target 100. Target 100 can be a structure configured to produce a desired result in response to the stimulus applied by the incident beam, or can modify the nature of the beam. Target 100 can be a component of system 10 or can be a workpiece that is conditioned or manufactured, at least in part, by system 10.

Figure 1B:
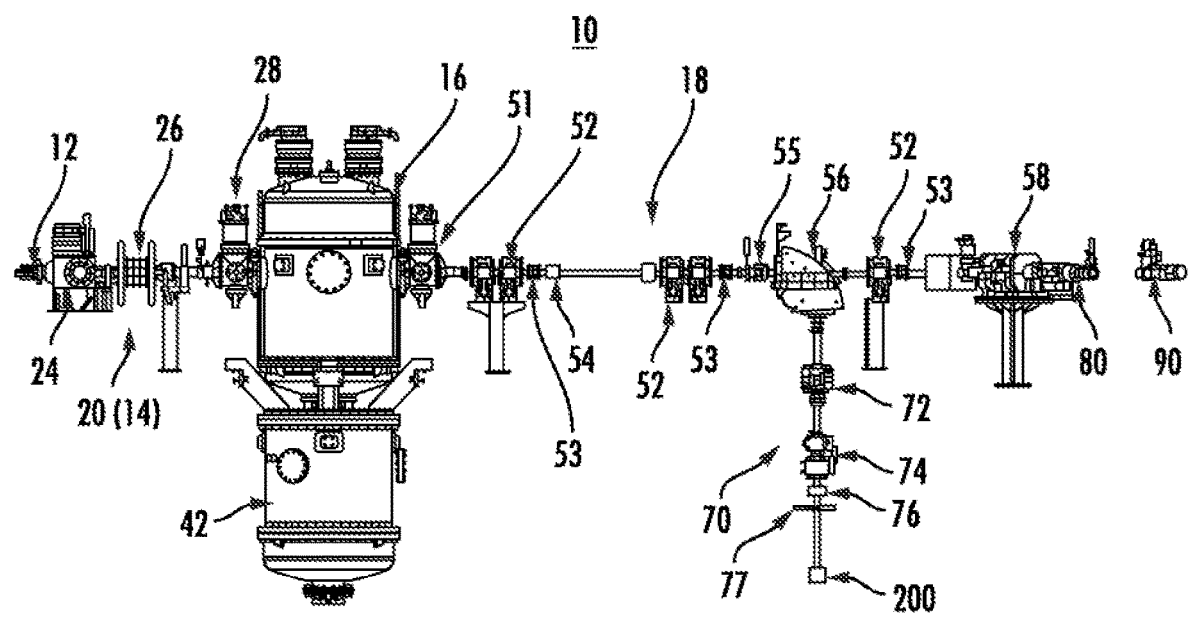
FIG. 1B is a schematic diagram of an example embodiment of a neutron beam system for use in boron neutron capture therapy (BNCT).

FIG. 1B is a schematic diagram illustrating another example embodiment of a neutron beam system 10 for use in boron neutron capture therapy (BNCT). Here, source 12 is an ion source and accelerator 16 is a tandem accelerator. Neutron beam system 10 includes a pre-accelerator system 20, serving as a charged particle beam injector, high voltage (HV) tandem accelerator 16 coupled to pre-accelerator system 20, and HEBL 18 extending from tandem accelerator 16 to a neutron target assembly 200 housing target 100 (not shown). In this embodiment target 100 is configured to generate neutrons in response to impact by protons of a sufficient energy, and can be referred to as a neutron generation target. Neutron beam system 10 as well as pre-accelerator system 20 can also be used for other applications such as those other examples described herein, and is not limited to BNCT.

Pre-accelerator system 20 is configured to transport the ion beam from ion source 12 to the input (e.g., an input aperture) of tandem accelerator 16, and thus also acts as LEBL 14. Tandem accelerator 16, which is powered by a high voltage power supply 42 coupled thereto, can produce a proton beam with an energy generally equal to twice the voltage applied to the accelerating electrodes positioned within accelerator 16. The energy level of the proton beam can be achieved by accelerating the beam of negative hydrogen ions from the input of accelerator 16 to the innermost high-potential electrode, stripping two electrons from each ion, and then accelerating the resulting protons downstream by the same applied voltage.

HEBL 18 can transfer the proton beam from the output of accelerator 16 to the target within neutron target assembly 200 positioned at the end of a branch 70 of the beamline extending into a patient treatment room. System 10 can be configured to direct the proton beam to any number of one or more targets and associated treatment areas. In this embodiment, the HEBL 18 includes three branches 70, 80 and 90 that can extend into three different patient treatment rooms, where each branch can terminate in a target assembly 200 and downstream beam shaping apparatus (not shown). HEBL 18 can include a pump chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, a fast beam position monitor 55 section, and a scanning magnet 74.

The design of HEBL 18 depends on the configuration of the treatment facility (e.g., a single-story configuration of a treatment facility, a two-story configuration of a treatment facility, and the like). The beam can be delivered to target assembly (e.g., positioned near a treatment room) 200 with the use of bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering scanning magnets 74, the beam can be delivered into a current monitor 76, which measures beam current. Target assembly 200 can be physically separated from the HEBL volume with a gate valve 77. The main function of the gate valve is separation of the vacuum volume of the beamline from the target while loading the target and/or exchanging a used target for a new one. In embodiments, the beam can not be bent by 90 degrees by a bending magnet 56, it rather goes straight to the right of FIG. 1B, then enters quadrupole magnets 52, which are located in the horizontal beamline. The beam could be subsequently bent by another bending magnet 58 to a needed angle, depending on the building and room configuration. Otherwise, bending magnet 58 could be replaced with a Y-shaped magnet in order to split the beamline into two directions for two different treatment rooms located on the same floor.

Figure 2:
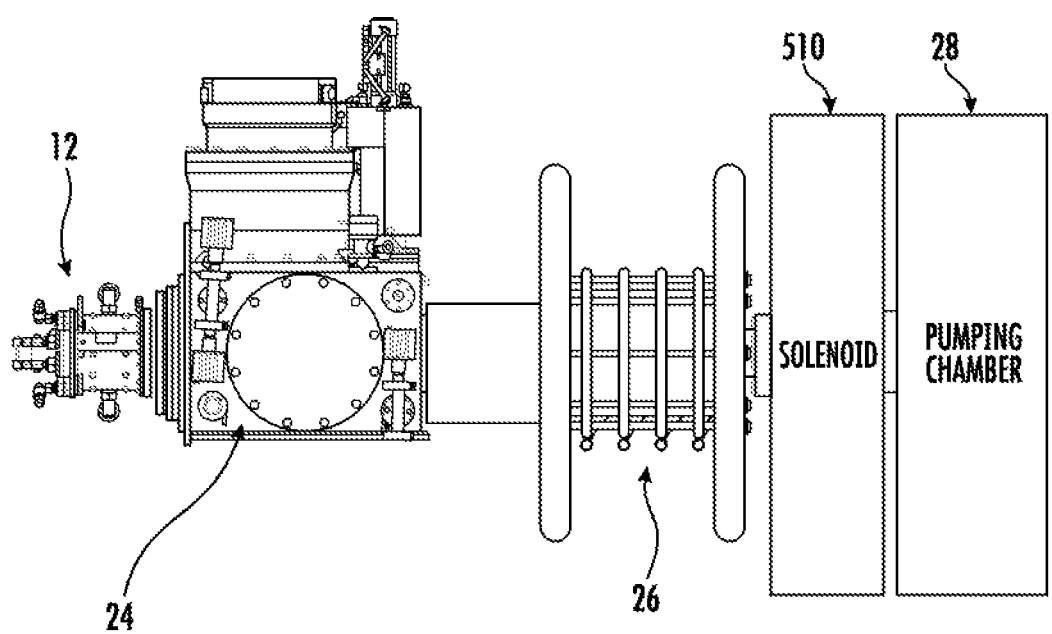
FIG. 2 illustrates an example pre-accelerator system or ion beam injector for use with embodiments of the present disclosure.

FIG. 2 illustrates an example of a pre-accelerator system or ion beam injector for use with embodiments of the present disclosure. In this example, pre-accelerator system 20 (e.g., LEBL 14) includes an einzel lens 30 (not visible in FIG. 2, but depicted in FIGS. 3A-3B), a pre-accelerator tube 26, and a solenoid 510, and is configured to accelerate a negative ion beam injected from ion source 12. The pre-accelerator system 20 is configured to provide acceleration of the beam particles to the energies required for tandem accelerator 16, and to provide overall convergence of the negative ion beam to match input aperture area at an input aperture or entrance of the tandem accelerator 16. The pre-accelerator system 20 is further configured to minimize or defocus backflow as it passes from the tandem accelerator 16 through the pre-accelerator system in order to reduce the possibility of damage to ion source 12 and/or the backflow reaching the filaments of the ion source.

In embodiments, the ion source 12 can be configured to provide a negative ion beam upstream of the einzel lens 30, and the negative ion beam continues to pass through pre-accelerator tube 26 and a magnetic focusing device (e.g., solenoid) 510. The solenoid 510 can be positioned between the pre-accelerator tube 26 and the tandem accelerator 16 and is electrically couplable with a power supply. The negative ion beam passes through the solenoid 510 to the tandem accelerator 16.

Pre-accelerator system 20 can also include an ion source vacuum box 24 for removing gas, and a pump chamber 28, which, with pre-accelerator tube 26 as well as the other elements described above are part of a relatively low energy beamline leading to the tandem accelerator 16. The ion source vacuum box 24, within which the einzel lens 30 can be positioned, extends from the ion source 12. The pre-accelerator tube 26 can be coupled to the ion source vacuum box 24 and to solenoid 510. A vacuum pump chamber 28 for removing gas can be coupled to the solenoid 510 and the tandem accelerator 16. The ion source 12 serves as a source of charged particles which can be accelerated, conditioned and eventually used to produce neutrons when delivered to a neutron producing target. The example embodiments will be described herein with reference to an ion source producing a negative hydrogen ion beam, although embodiments are not limited to such, and other positive or negative particles can be produced by the source.

The pre-accelerator system 20 can have zero, one, or multiple magnetic elements for purposes such as focusing and/or adjusting alignment of the beam. For example, any such magnetic elements can be used to match the beam to the beamline axis and the acceptance angle of the tandem accelerator 16. The ion vacuum box 24 can have ion optics positioned therein.

There are generally two types of negative ion sources 12, which differ by the mechanism of generation of negative ions: the surface type and the volume type. The surface type generally requires the presence of cesium (Cs) on specific internal surfaces. The volume type relies on formation of negative ions in the volume of a high current discharge plasma. While both types of ion sources can deliver the desired negative ion current for applications related to tandem accelerators, surface type negative ion sources are undesirable for modulation. That is, for modulation of a negative ion beam in embodiments described herein, negative ion sources of the volume type (e.g., without employing cesium (Cs)) are preferred.

Figure 3A:
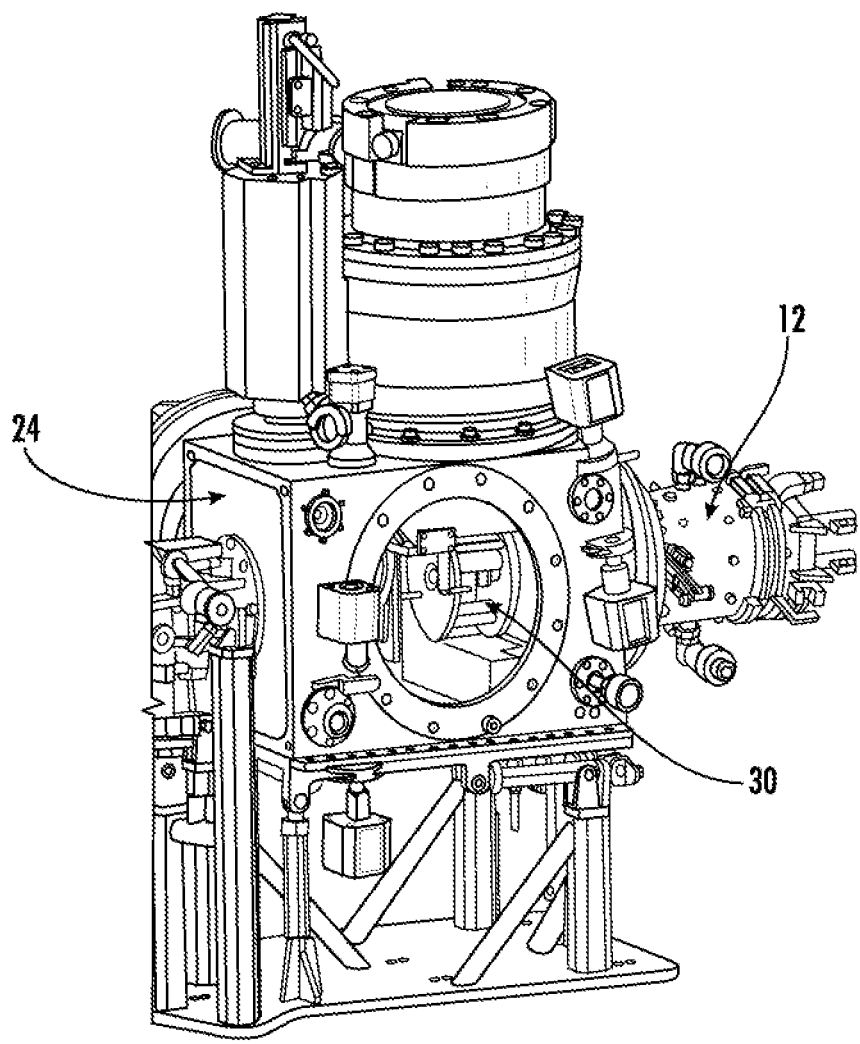
FIG. 3A is a perspective view of the ion source and the ion source vacuum box shown in FIG. 2.
Figure 3B:
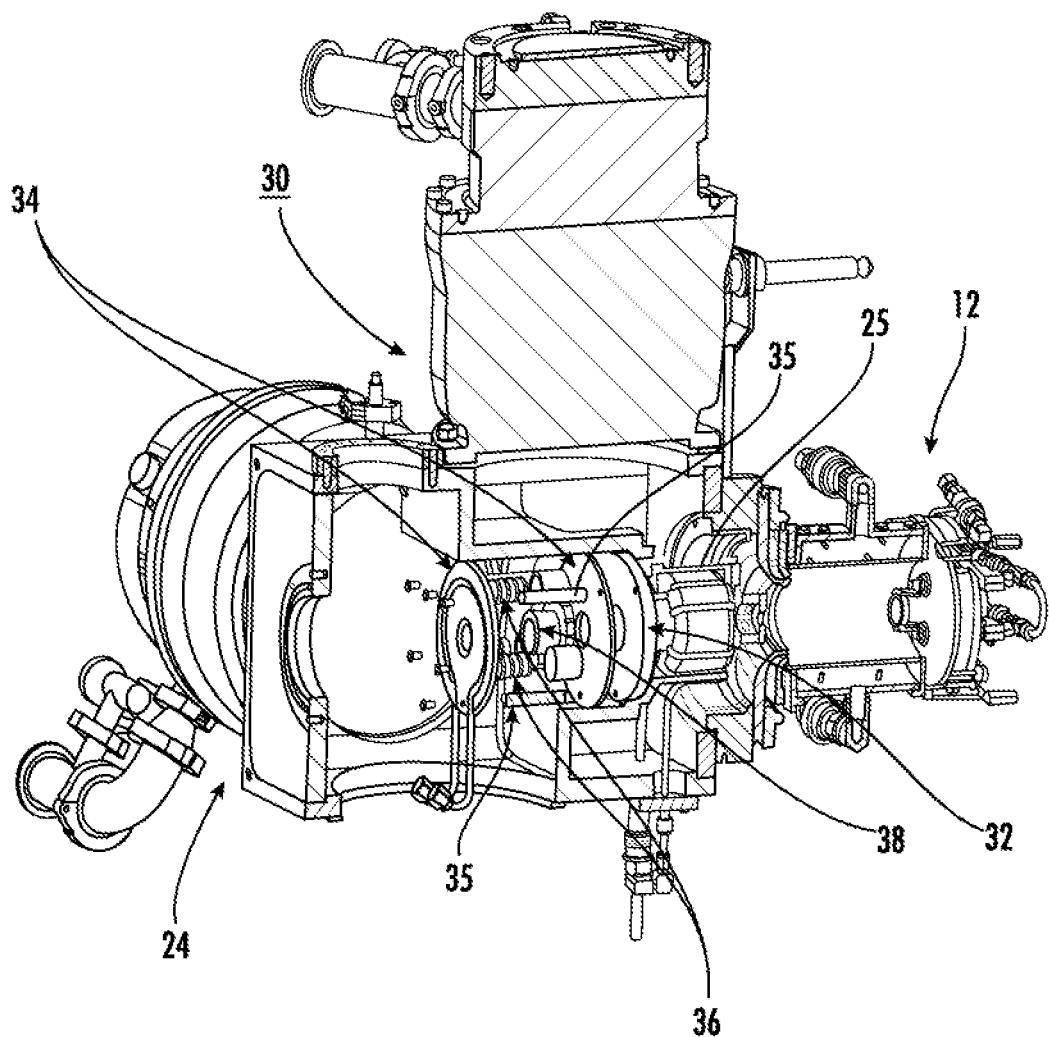
FIG. 3B is an exploded perspective view depicting an example embodiment of the einzel lens shown in FIG. 3A.

Turning to FIG. 3A, the ion source vacuum box 24 of the ion beam injector 20 includes an einzel lens 30 positioned therein. As shown in detail in FIG. 3B, the einzel lens 30, which is mounted downstream of a ground lens 25 of the ion source 12 within the vacuum box 24, includes a mounting plate 32, two grounded electrodes 34 mounted to the mounting plate 32 and coupled to one of another in spaced relation with mounting rods 35, and a powered (biased) electrode 38 positioned between the two grounded electrodes 34. The electrodes 34 and 38 are made in the form of cylindrical apertures and assembled to have an axial axis coinciding with the beam path. The powered electrode 38 is supported by insulators/isolators 36 extending between the grounded electrodes or apertures 34.

The standoff isolators 36 can include a geometric design configured to inhibit development of electron avalanches and to suppress streamer formation and propagation which is typically ending up in a flashover formation. The geometric design of standoff isolators 36 can partially screen an external electric field on the insulator surface which drives the electron avalanche and effectively increases the path length. In addition, the materials of insulators/isolators 36 tend to diminish sputtering effects, loss of negative ions on surfaces, volume contamination, and formation of a conductive coating on the insulator/isolator surfaces leading to a decrease of electrical strength.

Functionally, action of the einzel lens 30 on the beam of charged particles advancing from the ion source 12 is akin to the action of optical focusing lens on a beam of light. Namely, the einzel lens 30 is focusing the incoming parallel beam into a spot at the focal plane. However, here the electric fields formed between the pairs of the powered electrode 38 and the two grounded electrodes 34 determine the focusing strength of the einzel lens (focal length distance).

By mounting the einzel lens 30 downstream of the ion source ground lens 25, it diminishes beam free space transportation where the beam is subjected to divergence due to intrinsic space charge.

The dimensions of the axisymmetric design of the einzel lens 30 are optimized to avoid direct interaction of extracted ions with exposed surfaces of the einzel lens 30.

In operation, negative polarity biasing of the einzel lens 30 results in higher focusing power over the positive bias polarity. Also in operation, the method of power delivery to the einzel lens 30 provides for gradual voltage growth instead of instantaneous voltage application, which reduces growth rates of electric field (dE/dt) at micro-protrusions existing on surfaces of the einzel lens 30 responsible for plasma formation via, for example, an explosive emission mechanism. Impeding of such plasma formation improves electrical strength.

Negative bias potential for an einzel lens in high background pressure is usually not possible due to electrical breakdowns. The configuration of the example embodiments of the einzel lens provided herein, enables the application of negative bias voltages sufficiently high for the 100% current utilization without electrical breakdowns.

Figure 4A:
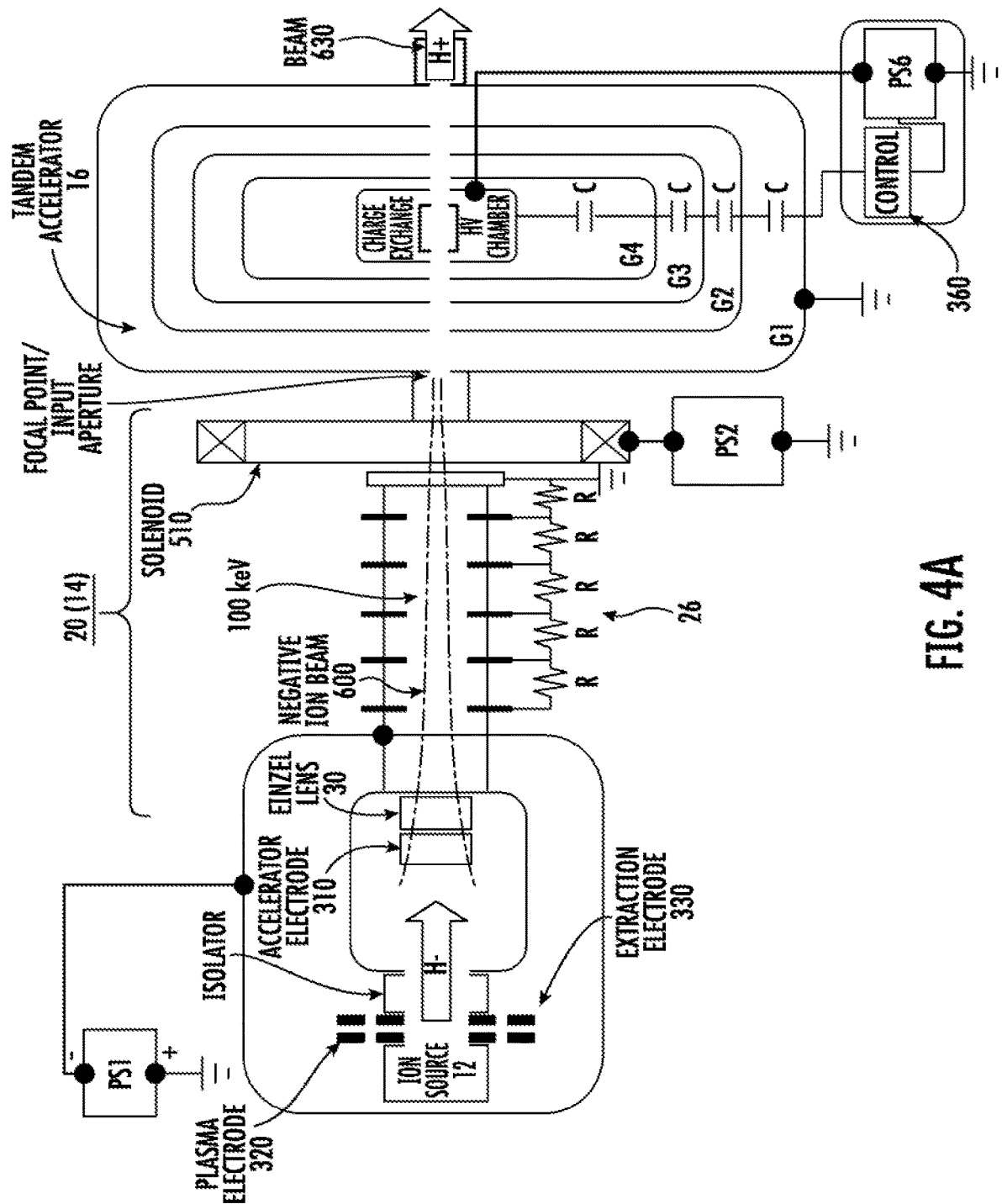
FIG. 4A illustrates an example ion beam source system, for use with embodiments of the present disclosure.

FIG. 4A illustrates an example ion beam source system, for use with embodiments of the present disclosure. In FIG. 4A, an ion source 12 is optionally housed in an ion source enclosure. The ion source 12 includes multiple electrodes, such as a plasma electrode 320, an accelerator/acceleration electrode (e.g., or ground lens) 310, and an extraction electrode 330. Optionally, ion source 12 is coupled with an einzel lens 30, and a negative ion beam is injected or propagated from the ion source 12 through the einzel lens 30, a pre-accelerator tube 26, and a solenoid 510 to an input aperture of a tandem accelerator 16.

Figure 4B:
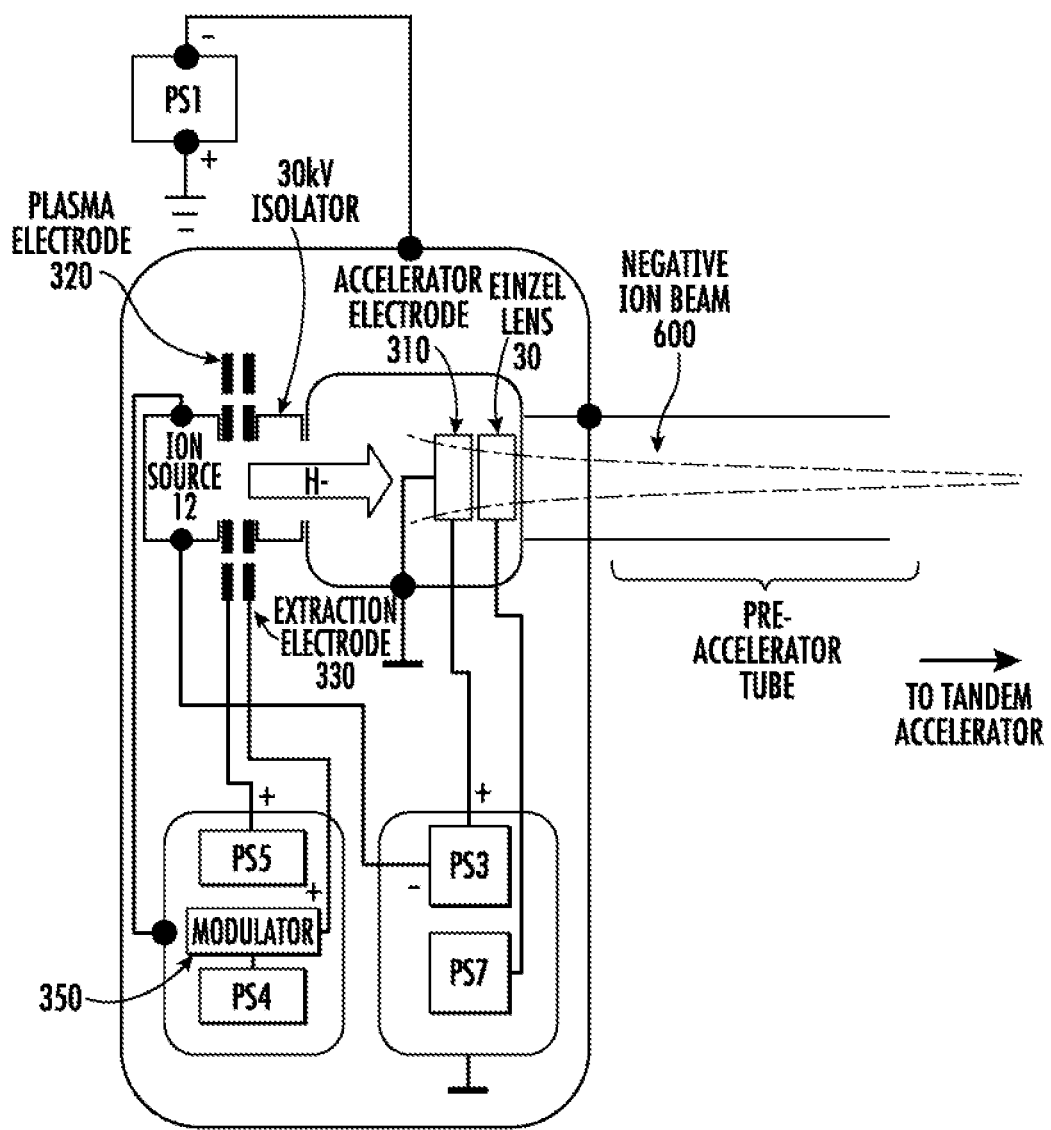
FIG. 4B illustrates an example ion source depicted in FIG. 4A.

Referring to FIG. 4B, ion source 12 can be electrically coupled, at accelerator electrode 310, with a first terminal of a power supply PS3, which is in turn electrically coupled at a second terminal to an enclosure of the ion source 12. Biasing of ion source 12 at accelerator electrode 310 configures the pre-accelerator system 20 for maintenance and passage of a negative ion beam when such a beam is passed from the ion source 12. In some embodiments, power supply PS3 can provide a voltage of −30 kV.

A plasma electrode 320 of ion source 12 can be electrically coupled to a power supply PS5 and an extraction electrode 330 of ion source 12 can be electrically coupled to a modulator 350 which is, in turn, electrically coupled to a power supply PS4. Biasing of plasma electrode 320 enables ion source 12 to maintain a plasma within the ion source 12 to be used for extraction into a negative ion beam when extraction electrode 330 is biased.

In some embodiments, modulator 350 and power supply PS4 can be combined within a single integrated moderator system. Modulator 350 includes a switch that can be used to control biasing of extraction electrode 330.

When extraction electrode 330 is biased, a negative ion beam is passed or propagated from ion source 12 along to the tandem accelerator 16. When extraction electrode 330 is not biased, a negative ion beam is not passed or propagated from ion source 12 along to the tandem accelerator 16.

As discussed above, tandem accelerator 16 is powered by a high voltage power supply 42 coupled thereto, and can produce a proton beam with an energy generally equal to twice the voltage applied to the accelerating electrodes positioned within accelerator 16. Tandem accelerator 16 can include any number of two or more nested shells with accelerating electrodes located at the leftmost and rightmost apertures of each shell as shown in FIG. 4A. In this embodiment, accelerator 16 includes four shells G1, G2, G3, G4 plus an innermost shell labeled as High Voltage (HV) Chamber. Power supply PS6 can be governed by a feedback loop whereby voltage stability within the tandem accelerator 16 is maintained. That is, a measurement or control device 360 (e.g., a voltmeter) can monitor a voltage across capacitors (C) installed in outputs of sections of a high voltage rectifier of the tandem accelerator 16. At least one capacitor can be connected between each shell and the shell(s) immediately adjacent thereto. In this example there are four capacitors connected across the five shells. Operation of the beam through accelerator 16 can lead to discharge of the capacitors. Voltage stability can dictate that a discharge of the capacitors cannot exceed a threshold of the fully charged state to maintain stability of the beam 620. In some embodiments this threshold is 5%, in other embodiments this threshold is 6%, in other embodiments this threshold is 10%, and in still other embodiments this threshold is 15%. In such examples, measurement or control device 360 can provide a feedback signal to power supply PS6 indicative of voltage instability, and power supply PS6 discontinues biasing tandem accelerator 16.

FIG. 5A illustrates an example desired steady state emission pulse of an ion beam source, for use with embodiments of the present disclosure. FIG. 5B illustrates an example undesirable steady state emission pulse of an ion beam source. Shown in FIG. 5A, biasing of an extraction electrode at an ion beam source results in a steady state extraction of negative hydrogen ions from the plasma of the ion source within a short period of time, otherwise production of the ion beam can be unsuccessful within the requisite window for protection of downstream components. FIG. 5B depicts an undesirable ramp up to steady state extraction.

FIG. 6A illustrates an example capacitive discharge curve, for use with embodiments of the present disclosure. FIG. 6B illustrates an example desired current pulse curve, for use with embodiments of the present disclosure. A desired ion beam pulse current signature resembles an ideal step function, with minimal rise and fall slopes and a constant value for the active duration of the pulse as shown in FIG. 6B, and leads to a capacitive discharge curve as shown in FIG. 6A, where modulation does not lead to a capacitive discharge exceeding a threshold (e.g., the threshold can be, in some embodiments, approximately 5-6%). As discussed above, limiting a duration of a pulse of a negative ion beam 600, by way of a modulator 350 or modulation system controlling the biasing (or not biasing) of an extraction electrode 330 of ion source 12, reduces the likelihood that the discharge of the multiple capacitors exceeds 5-6% and thereby reduces the likelihood (or eliminates entirely) the power supply PS6 discontinuing power to the tandem accelerator 16.

The capacitive rating of the multiple capacitors can contribute to a limit on a successful beam pulse duration. That is, the larger the capacitors, the longer a beam pulse duration can possibly be, however space and other design constraints lead to a lack of flexibility when it comes to increasing capacitance in various beam systems.

Figure 7:
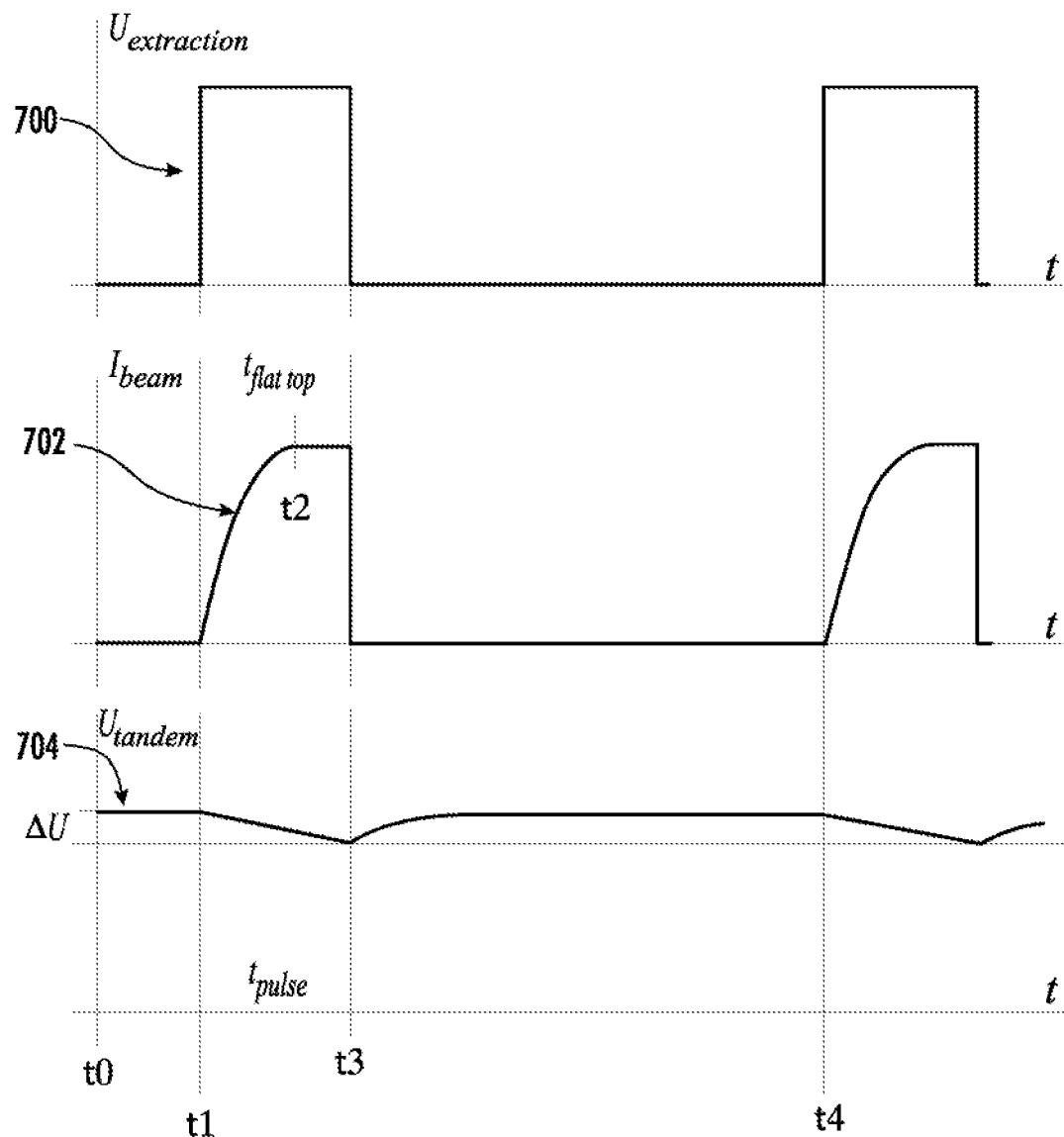
FIG. 7 is a timing diagram of an example biasing scheme for use with embodiments of the present disclosure.

FIG. 7 is a timing diagram showing examples of various parameters in temporal relationship to each other for use with embodiments of the present disclosure. In the uppermost diagram of FIG. 7, an extraction bias is applied (e.g., $U_{extraction}$) for a given duration from t1 to t3 (e.g., $t_{pulse}$) to form an extraction pulse 700 that causes extraction of a beam from the particle source. As shown here the extraction bias is applied in the shape of a step function or square wave, although this is an idealized depiction and those of ordinary skill in the art will recognize that some deviation will occur. The current of the extracted beam ($I_{beam}$) is depicted in the middle diagram. The current $I_{beam}$ responds to the extraction bias $U_{extraction}$ by increasing rapidly from t1 until reaching a constant, or substantially constant magnitude at t2. This is depicted by the flat or substantially flat uppermost contour of the current pulse 702. This region of steady magnitude can be referred to as the steady state of the current, and persists for a duration (e.g., $t_{flat\ top}$) until the extraction bias is removed at t3. In certain embodiments, the steady state duration of time t2 to t3 (e.g., $t_{flat\ top}$) is sufficiently long for one or more measurements associated with the beam system to be obtained.

Prior to beam extraction (e.g., from t0 to t1), an accelerator voltage $U_{tandem}$ is charged to a steady state level 704. In the embodiment of a tandem accelerator 16 described with respect to FIG. 4A, this steady state level can be a full charge to the capacitors (C) between respective accelerating electrodes. When beam extraction begins from the ion source at t1, a discharge of a these capacitors can occur. In these embodiments, the discharge is preferably maintained within a discharge threshold ΔU (e.g., 15% or less, 10% or less, 6% or less). In some embodiments, the modulation system can be set or programmed such that the duration of $t_{pulse}$ is a time length that maintains the discharge amount within the threshold ΔU. In some embodiments, the duration of $t_{pulse}$ can be controlled with a feedback loop, such that the discharge amount is actively monitored by the modulation system (or by the control systems described herein) and the extraction pulse is terminated before the discharge amount (or conversely before $U_{tandem}$ drops or decreases below) the discharge threshold ΔU. When extraction pulse 700 is terminated at t3 such that the beam is no longer extracted from the example ion source, the charge of the capacitors (e.g., $U_{tandem}$) returns to nominal level 704. In embodiments, the minimal period (e.g., t1 to t4) of the charge pulses is sufficient to exceed the duration to charge the capacitors back to level 704.

Figure 8:
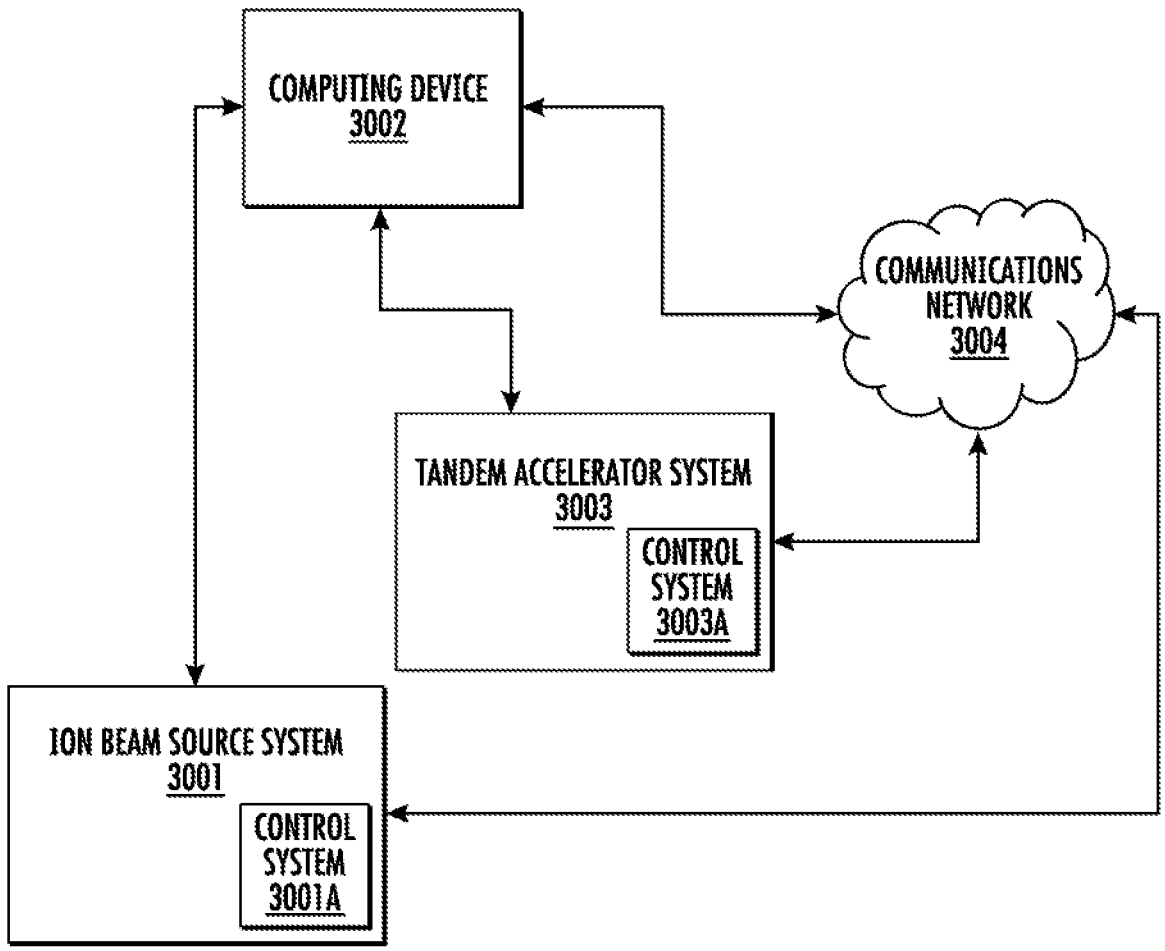
FIG. 8 illustrates a block diagram of a system within which embodiments of the present disclosure can operate.

FIG. 8 is a block diagram showing an example system within which embodiments of the present disclosure can operate. For example, the illustrated example system includes an ion beam source system 3001, one or more computing devices 3002, and a tandem accelerator system 3003. In embodiments, ion beam source system 3001 and tandem accelerator system 3003 can collectively be part of an example neutron beam system (e.g., system 10 above). In such embodiments, the neutron beam system 10 can employ one or more control systems with which one or more computing device 3002 can communicate in order to interact with the systems and components of the neutron beam system 10. Each of these devices and/or systems are configured to communicate directly with one another (not shown) or via a local network, such as network 3004.

Computing devices 3002 can be embodied by various user devices, systems, computing apparatuses, and the like. For example, a first computing device 3002 can be a desktop computer associated with a particular user, while another computing device 3002 can be a laptop computer associated with a particular user, and yet another computing device 3002 can be a mobile device (e.g., a tablet or smart device). Each of the computing devices 3002 can be configured to communicate with the ion beam source system 3001 and/or tandem accelerator system 3003, for example through a user interface accessible via the computing device. For example, a user can execute a desktop application on the computing device 3002, which is configured to communicate with the ion beam source system 3001 and/or tandem accelerator system 3003.

By using a computing device 3002 to communicate with one or more of the ion beam source system 3001 or tandem accelerator system 3003, a user can provide operating parameters for either of the systems (e.g., operating voltages, and the like) according to embodiments described herein. In embodiments, ion beam source system 3001 can include a control system 3001A by which ion beam source system 3001 can receive and apply operating parameters from computing device 3002. In embodiments, tandem accelerator system 3003 can include a control system 3003A by which tandem accelerator system 3003 can receive and apply operating parameters from computing device 3002.

Communications network 3004 can include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 3004 can include an 802.11, 802.16, 802.20, and/or WiMax network. Further, the communications network 3004 can include a public network, such as the Internet, a private network, such as an intranet, or combinations thereof, and can utilize a variety of networking protocols now available or later developed including, but not limited to TCP/IP based networking protocols.

Figure 9:
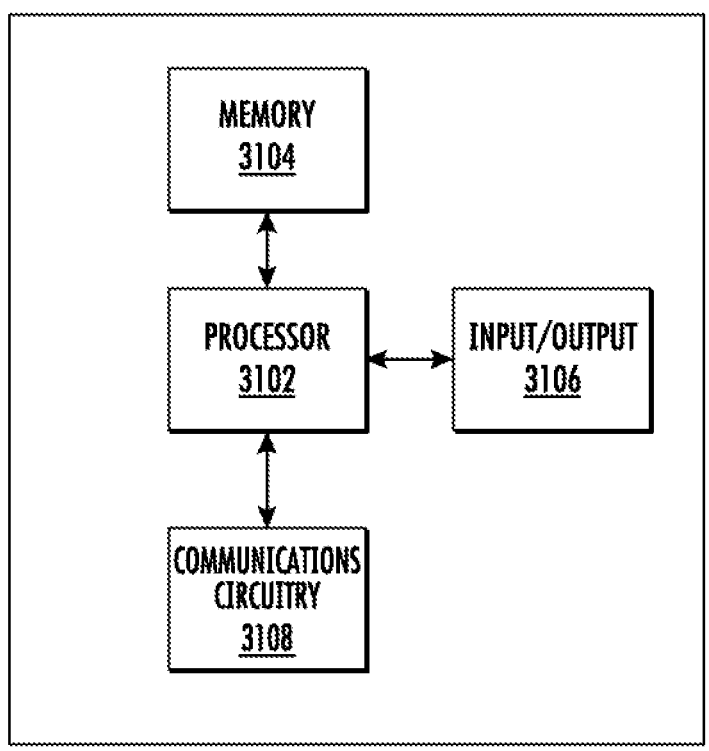
FIG. 9 illustrates an example computing apparatus that can be specially configured in accordance with embodiments of the present disclosure.

The computing device 3002 and control systems 3001A and 3003A can be embodied by one or more computing systems, such as apparatus 3100 shown in FIG. 9. As illustrated in FIG. 9, the apparatus 3100 can include a processor 3102, a memory 3104, an input and/or output circuitry 3106, and communications device or circuitry 3108 It should also be understood that certain of these components 3102-3108 can include similar hardware. For example, two modules can both leverage use of the same processor, network interface, storage medium, or the like to perform their associated functions, such that duplicate hardware is not required for each device. The use of the terms "device" and/or "circuitry" as used herein with respect to components of the apparatus therefore can encompass particular hardware configured with software to perform the functions associated with that particular device, as described herein.

The terms "device" and/or "circuitry" should be understood broadly to include hardware, in some embodiments, device and/or circuitry can also include software for configuring the hardware. For example, in some embodiments, device and/or circuitry can include processing circuitry, storage media, network interfaces, input/output devices, and the like. In some embodiments, other elements of the apparatus 3100 can provide or supplement the functionality of particular device(s). For example, the processor 3102 can provide processing functionality, the memory 3104 can provide storage functionality, the communications device or circuitry 3108 can provide network interface functionality, and the like.

In some embodiments, the processor 3102 (and/or coprocessor or any other processing circuitry assisting or otherwise associated with the processor) can be in communication with the memory 3104 via a bus for passing information among components of the apparatus. The memory 3104 can be non-transitory and can include, for example, one or more volatile and/or non-volatile memories. In other words, for example, the memory can be an electronic storage device (e.g., a computer readable storage medium.) The memory 3104 can be configured to store information, data, content, applications, instructions, or the like, for enabling the apparatus to carry out various functions in accordance with example embodiments of the present disclosure.

The processor 3102 can be embodied in a number of different ways and may, for example, include one or more processing devices configured to perform independently. Additionally or alternatively, the processor can include one or more processors configured in tandem via a bus to enable independent execution of instructions, pipelining, and/or multithreading. The use of the terms "processing device" and/or "processing circuitry" can be understood to include a single core processor, a multi-core processor, multiple processors internal to the apparatus, and/or remote or "cloud" processors.

In an example embodiment, the processor 3102 can be configured to execute instructions stored in the memory 3104 or otherwise accessible to the processor. Alternatively or additionally, the processor can be configured to execute hard-coded functionality. As such, whether configured by hardware or software methods, or by a combination of hardware with software, the processor can represent an entity (e.g., physically embodied in circuitry) capable of performing operations according to an embodiment of the present disclosure while configured accordingly. Alternatively, as another example, when the processor is embodied as an executor of software instructions, the instructions can specifically configure the processor to perform the algorithms and/or operations described herein when the instructions are executed.

In some embodiments, the apparatus 3100 can include input/output device 3106 that may, in turn, be in communication with processor 3102 to provide output to the user and, in some embodiments, to receive input from the user. The input/output device 3106 can include a user interface and can include a device display, such as a user device display, that can include a web user interface, a mobile application, a client device, or the like. In some embodiments, the input/output device 3106 can also include a keyboard, a mouse, a joystick, a touch screen, touch areas, soft keys, a microphone, a speaker, or other input/output mechanisms. The processor and/or user interface circuitry including the processor can be configured to control one or more functions of one or more user interface elements through computer program instructions (e.g., software and/or firmware) stored on a memory accessible to the processor (e.g., memory 3104, and/or the like).

The communications device or circuitry 3108 can be any means such as a device circuitry embodied in either hardware or a combination of hardware and software that is configured to receive and/or transmit data from/to a network and/or any other device or circuitry in communication with the apparatus 3100. In this regard, the communications device or circuitry 3108 can include, for example, a network interface for enabling communications with a wired or wireless communication network. For example, the communications device or circuitry 3108 can include one or more network interface cards, antennas, buses, switches, routers, modems, and supporting hardware and/or software, or any other device suitable for enabling communications via a network. Additionally or alternatively, the communication interface can include the circuitry for interacting with the antenna(s) to cause transmission of signals via the antenna(s) or to handle receipt of signals received via the antenna(s). These signals can be transmitted by the apparatus 3100 using any of a number of wireless personal area network (PAN) technologies, such as current and future Bluetooth standards (including Bluetooth and Bluetooth Low Energy (BLE)), infrared wireless (e.g., IrDA), FREC, ultra-wideband (UWB), induction wireless transmission, or the like. In addition, it should be understood that these signals can be transmitted using Wi-Fi, Near Field Communications (NFC), Worldwide Interoperability for Microwave Access (WiMAX), or other proximity-based communications protocols.

As will be appreciated, any such computer program instructions and/or other type of code can be loaded onto a computer, processor, or other programmable apparatus' circuitry to produce a machine, such that the computer, processor, or other programmable circuitry that executes the code on the machine creates the means for implementing various functions, including those described herein.

As described above and as will be appreciated based on this disclosure, embodiments of the present disclosure can be configured as systems, methods, mobile devices, backend network devices, and the like. Accordingly, embodiments can include various implementations including entirely of hardware or any combination of software and hardware. Furthermore, embodiments can take the form of a computer program product on at least one non-transitory computer-readable storage medium having computer-readable program instructions (e.g., computer software) embodied in the storage medium. Any suitable computer-readable storage medium can be utilized including non-transitory hard disks, CD-ROMs, flash memory, optical storage devices, or magnetic storage devices.

Processing circuitry for use with embodiments of the present disclosure can include one or more processors, microprocessors, controllers, and/or microcontrollers, each of which can be a discrete chip or distributed amongst (and a portion of) a number of different chips. Processing circuitry for use with embodiments of the present disclosure can include a digital signal processor, which can be implemented in hardware and/or software of the processing circuitry for use with embodiments of the present disclosure. Processing circuitry for use with embodiments of the present disclosure can be communicatively coupled with the other components of the figures herein. Processing circuitry for use with embodiments of the present disclosure can execute software instructions stored on memory that cause the processing circuitry to take a host of different actions and control the other components in figures herein.

Memory for use with embodiments of the present disclosure can be shared by one or more of the various functional units, or can be distributed amongst two or more of them (e.g., as separate memories present within different chips). Memory can also be a separate chip of its own. Memory can be non-transitory, and can be volatile (e.g., RAM, etc.) and/or non-volatile memory (e.g., ROM, flash memory, F-RAM, etc.).

Computer program instructions for carrying out operations in accordance with the described subject matter can be written in any combination of one or more programming languages, including an object oriented programming language such as Java, JavaScript, Smalltalk, C++, C#, Transact-SQL, XML, PHP or the like and conventional procedural programming languages, such as the "C" programming language or similar programming languages.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many embodiments, an ion beam system includes an ion source configured to provide a negative ion beam to a tandem accelerator system downstream of the ion source and a modulator system connected to an extraction electrode of the ion source. In many of these embodiments, the modulator system is configured to bias the extraction electrode for a duration sufficient to achieve steady state ion extraction and maintain acceleration voltage stability of the tandem accelerator system.

In many of these embodiments, the ion source is configured to generate negative hydrogen ions.

In many of these embodiments, the duration is less than 10 milliseconds (ms). In many of these embodiments, the duration is in a range of 0.5 to 1.0 milliseconds (ms).

In many of these embodiments, the modulator system includes a switch. In many of these embodiments, the modulator system includes a DC power supply.

In many of these embodiments, the acceleration voltage stability is based in part on capacitive discharge associated with multiple capacitors of the tandem accelerator system.

In many of these embodiments, one of an electrode or multiple electrodes of the tandem accelerator system is biased using a DC power supply. In many of these embodiments, the DC power supply is responsive to a feedback loop based on based on capacitive discharge associated with multiple capacitors within the tandem accelerator system. In many of these embodiments, the DC power supply includes an extra low voltage (ELV) DC power supply. In many of these embodiments, the duration is less than a response time of the feedback loop.

In many of these embodiments, the ion source includes an acceleration electrode. In many of these embodiments, the acceleration electrode is continuously biased using a first power supply.

In many of these embodiments, the ion source includes a plasma electrode. In many of these embodiments, the plasma electrode is continuously biased using a second power supply.

In many of these embodiments, the first power supply, the second power supply, and a third power supply of the modulator system are independent of one another.

In many of these embodiments, the negative ion beam passes through a pre-accelerator system downstream from the ion beam source system before reaching the tandem accelerator system. In many of these embodiments, the duration is sufficiently short to avoid beam induced damage to components of the pre-accelerator system or the tandem accelerator system.

In many of these embodiments, the duration is sufficient to enable provision of a proton beam having a beam energy of 2.5 megaelectronvolts (MeV).

In many of these embodiments, the duration is sufficient such that capacitive discharge within the tandem accelerator system of less than 15% occurs as a result of an introduction of the negative ion beam.

In many of these embodiments, the duration is sufficient such that capacitive discharge within the tandem accelerator system of less than 6% occurs as a result of an introduction of the negative ion beam.

In many of these embodiments, the duration is sufficiently long to enable a steady state ion extraction from the ion source. In many of these embodiments, a steady state ion extraction ramp-up time for the ion source is 0.1-0.3 milliseconds (ms).

In many of these embodiments, the tandem accelerator system includes multiple input electrodes, a charge exchange device, and multiple output electrodes. In many of these embodiments, the multiple input electrodes are configured to accelerate a negative ion beam from a pre-accelerator system, the charge exchange device is configured to convert the negative ion beam to a positive beam, and the multiple output electrodes are configured to accelerate the positive beam. In many of these embodiments, a target device downstream from the tandem accelerator system is configured to form a neutral beam from the positive beam received from the tandem accelerator system. In many of these embodiments, the duration is short enough to avoid beam induced damage to the target device.

In many embodiments, a method of beam modulation includes biasing an extraction electrode of an ion source for a duration sufficient to maintain an acceleration voltage stability of a tandem accelerator system to which the ion source is configured to provide a negative ion beam.

In many of these embodiments, the ion source is configured to generate negative hydrogen ions.

In many of these embodiments, the method includes biasing the extraction electrode for less than 10 milliseconds (ms). In many of these embodiments, the method includes biasing the extraction electrode for between 0.5 to 1 milliseconds (ms).

In many of these embodiments, the method includes measuring the acceleration voltage stability based in part on capacitive discharge associated with multiple capacitors of the tandem accelerator system.

In many of these embodiments, the method includes biasing one of an electrode or multiple electrodes of the tandem accelerator system using a DC power supply.

In many of these embodiments, the DC power supply is responsive to a feedback loop based on based on capacitive discharge associated with multiple capacitors within the tandem accelerator system.

In many of these embodiments, the method includes biasing the extraction electrode for a duration less than a response time of the feedback loop.

In many of these embodiments, the ion source includes an acceleration electrode. In many of these embodiments, the method includes continuously biasing the acceleration electrode using a first power supply.

In many of these embodiments, the ion source includes a plasma electrode. In many of these embodiments, the method includes continuously biasing the plasma electrode using a second power supply.

In many of these embodiments, the negative ion beam passes through a pre-accelerator system downstream from the ion source before reaching the tandem accelerator system. In many of these embodiments, the duration is sufficiently short to avoid beam induced damage to components of the pre-accelerator system or the tandem accelerator system.

In many of these embodiments, the duration is sufficient to enable provision of a proton beam having a beam energy of 2.5 megaelectronvolts (MeV).

In many of these embodiments, the duration is sufficient such that capacitive discharge within the tandem accelerator system of no more than 6% occurs as a result of an introduction of the negative ion beam.

In many of these embodiments, the ion source includes a non-cesiated ion source.

In many of these embodiments, the duration is sufficiently long to enable a steady state ion extraction from the ion source. In many of these embodiments, a steady state ion extraction ramp-up time for the ion source is 0.1 milliseconds (ms)-0.3 milliseconds (ms).

In many embodiments, a beam system includes a source including an extraction electrode, the source configured to generate a charged particle beam, a modulator system connected to an extraction electrode of the source, where the modulator system is configured to modulate the charged particle beam, and an accelerator configured to accelerate the modulated charged particle beam.

In many of these embodiments, the modulator system is configured to modulate the charged particle beam into multiple pulses. In many of these embodiments, each pulse has a duration sufficient to achieve steady state particle extraction.

In many of these embodiments, the accelerator includes one or more capacitors. In many of these embodiments, the modulated beam does not cause the one or more capacitors to discharge more than a threshold amount. In many of these embodiments, the threshold amount is 15% or less of a full charge of the one or more capacitors. In many of these embodiments, the threshold amount is 6% or less of a full charge of the one or more capacitors.

In many of these embodiments, the duration is less than 10 milliseconds (ms) and the duty cycle is between 0.1 and 10%.

In many of these embodiments, the duration is in a range of 0.5 to 1.0 milliseconds (ms).

In many of these embodiments, the modulator system is configured to modulate the charged particle beam to maintain acceleration voltage stability of the accelerator.

In many of these embodiments, the acceleration voltage stability is based at least in part on capacitive discharge associated with multiple capacitors of the accelerator.

In many of these embodiments, one of an electrode or multiple electrodes of the accelerator is biased using a DC power supply. In many of these embodiments, the DC power supply is responsive to a feedback loop based on capacitive discharge associated with multiple capacitors within the accelerator. In many of these embodiments, the duration is less than a response time of the feedback loop. In many of these embodiments, the accelerator is a tandem accelerator.

In many of these embodiments, the charged particle beam is a negative ion beam, the accelerator is configured to convert the negative ion beam to a proton beam, and each pulse has a duration sufficient to enable provision of the proton beam having a beam energy of between 1.9 and 3.0 megaelectron volts (MeV).

In many of these embodiments, the modulation system is configured to modulate the charged particle beam such that capacitive discharge within the accelerator does not exceed 15% during acceleration of the modulated charged particle beam.

In many of these embodiments, the modulation system is configured to modulate the charged particle beam such that capacitive discharge within the accelerator does not exceed 6% during acceleration of the modulated charged particle beam.

In many of these embodiments, the accelerator is a tandem accelerator including multiple nested shells and one or more capacitors electrically coupled between adjacent shells, and the capacitive discharge is discharge of the one or more capacitors.

In many of these embodiments, the accelerator is a tandem accelerator including multiple input electrodes, a charge exchange device, and multiple output electrodes. In many of these embodiments, the charged particle beam is a negative ion beam, and the tandem accelerator is configured to accelerate the negative ion beam with the multiple input electrodes, the charge exchange device is configured to convert the negative ion beam to a positive beam, and the tandem accelerator is configured to accelerate the positive beam with the multiple output electrodes. In many of these embodiments, the beam system includes a target device downstream from the tandem accelerator. In many of these embodiments, the target device is configured to form a neutral beam from the positive beam.

In many of these embodiments, the modulator system is configured to modulate the charged particle beam into multiple pulses. In many of these embodiments, each pulse has a duration limited to avoid thermal damage to the target device.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An ion beam source system, comprising:
   a tandem accelerator system downstream of an ion source and comprising a plurality of capacitors;
   the ion source, wherein the ion source is configured to provide a negative ion beam to the tandem accelerator system downstream; and
   a modulator system connected to an extraction electrode of the ion source, wherein the modulator system is configured to:
   bias the extraction electrode until steady state ion extraction and acceleration voltage stability of the tandem accelerator system is achieved; and
   discontinue biasing the extraction electrode when a measured voltage across two or more of the plurality of capacitors of the tandem accelerator system is reduced below a threshold.

2. The ion beam source system of claim 1, wherein the ion source is configured to generate negative hydrogen ions.

3. The ion beam source system of claim 1, wherein a duration occurs between biasing the extraction electrode and discontinuing biasing of the extraction electrode, and wherein the duration is less than 10 milliseconds (ms) or in a range of 0.5 ms to 1.0 ms.

4. The ion beam source system of claim 1, wherein the modulator system comprises one or more of a switch or a DC power supply.

5. The ion beam source system of claim 1, wherein acceleration voltage stability of the tandem accelerator system is based in part on capacitive discharge associated with the plurality of capacitors.

6. The ion beam source system of claim 1, wherein one or more of a plurality of electrodes of the tandem accelerator system is configured to be biased using a DC power supply.

7. The ion beam source system of claim 6, wherein the DC power supply is responsive to a feedback loop based on capacitive discharge associated with the plurality of capacitors of the tandem accelerator system.

8. The ion beam source system of claim 7, wherein a duration occurs between biasing the extraction electrode and discontinuing biasing the extraction electrode, and wherein the duration is less than a response time of the feedback loop.

9. The ion beam source system of claim 6, wherein the DC power supply comprises an extra low voltage (ELV) DC power supply.

10. The ion beam source system of claim 1, wherein the ion source comprises an acceleration electrode and wherein the acceleration electrode is configured to be continuously biased using a first power supply.

11. The ion beam source system of claim 1, wherein the ion source comprises a plasma electrode and wherein the plasma electrode is configured to be continuously biased using a second power supply.

12. The ion beam source system of claim 1, wherein the negative ion beam passes through a pre-accelerator system downstream from the ion beam source system before reaching the tandem accelerator system.

13. The ion beam source system of claim 12, wherein a duration occurs between biasing the extraction electrode and discontinuing biasing the extraction electrode, and wherein the duration is sufficiently short to avoid beam induced damage to components of the pre-accelerator system or the tandem accelerator system.

14. The ion beam source system of claim 1, wherein a duration occurs between biasing the extraction electrode and discontinuing biasing the extraction electrode, and wherein the duration is sufficient to enable provision of a proton beam having a beam energy of 2.5 megaelectronvolts (MeV).

15. The ion beam source system of claim 1, wherein a duration occurs between biasing the extraction electrode and discontinuing biasing the extraction electrode, and wherein the duration is sufficient such that capacitive discharge within the tandem accelerator system of less than 15% occurs as a result of an introduction of the negative ion beam.

16. The ion beam source system of claim 1, wherein a duration occurs between biasing the extraction electrode and discontinuing biasing the extraction electrode, and wherein the duration is sufficient such that capacitive discharge within the tandem accelerator system of less than 6% occurs as a result of an introduction of the negative ion beam.

17. The ion beam source system of claim 1, wherein a duration occurs between biasing the extraction electrode and discontinuing biasing the extraction electrode, and wherein the duration is sufficiently long to enable a steady state ion extraction from the ion source.

18. The ion beam source system of claim 17, wherein a steady state ion extraction ramp-up time for the ion source is 0.1-0.3 milliseconds (ms).

19. The ion beam source system of claim 1, wherein the tandem accelerator system comprises a plurality of input electrodes, a charge exchange device, and a plurality of output electrodes, wherein the plurality of input electrodes is configured to accelerate a negative ion beam from a pre-accelerator system, the charge exchange device is configured to convert the negative ion beam to a positive beam, and the plurality of output electrodes are configured to accelerate the positive beam.

20. The ion beam source system of claim 19, wherein a target device downstream from the tandem accelerator system is configured to form a neutral beam from the positive beam received from the tandem accelerator system, wherein a duration occurs between biasing the extraction electrode and discontinuing biasing the extraction electrode, and wherein the duration is short enough to avoid beam induced damage to the target device.

\* \* \* \* \*